(12) United States Patent
Petäjä et al.

(10) Patent No.: US 10,549,119 B2
(45) Date of Patent: Feb. 4, 2020

(54) METHOD AND APPARATUS PERTAINING TO OPTIMIZING A RADIATION-TREATMENT PLAN BY PERMITTING NON-COINCIDENTAL ISOCENTERS

(71) Applicant: Varian Medical Systems International AG, Steinhausen (CH)

(72) Inventors: Viljo Petäjä, Espoo (FI); Perttu Niemelä, Espoo (FI); Esa Kuusela, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 0 days.

(21) Appl. No.: 16/255,086

(22) Filed: Jan. 23, 2019

(65) Prior Publication Data

US 2019/0151680 A1 May 23, 2019

Related U.S. Application Data

(63) Continuation of application No. 15/080,685, filed on Mar. 25, 2016, now Pat. No. 10,226,643.

(51) Int. Cl.
*A61N 5/10* (2006.01)
*G16H 10/60* (2018.01)

(52) U.S. Cl.
CPC ........... *A61N 5/1031* (2013.01); *G16H 10/60* (2018.01); *A61N 5/1045* (2013.01)

(58) Field of Classification Search
None
See application file for complete search history.

(56) References Cited

U.S. PATENT DOCUMENTS

| 10,226,643 | B2 * | 3/2019 | Petaja | ................ A61N 5/1031 |
| 2011/0033028 | A1 | 2/2011 | Parsai et al. | |
| 2013/0150646 | A1 | 6/2013 | Scholz | |

* cited by examiner

*Primary Examiner* — Hoon K Song
(74) *Attorney, Agent, or Firm* — Fitch, Even, Tabin & Flannery LLP

(57) ABSTRACT

A control circuit utilizes patient information and treatment-platform information to optimize a radiation-treatment plan by permitting isocenters of various radiation-treatment fields as comprise parts of a same treatment plan to not be coincidental with one another to thereby yield an optimized treatment plan. The patient information can pertain to one or more physical aspects of the patient as desired. By one approach, the foregoing can comprise scattering the isocenters of the various radiation-treatment fields around a predetermined point (such as, for example, the center of the treatment volume and/or some or all of the beams). This approach can comprise causing an area of highest energy flux for a given field to be non-coincident for at least some of the radiation-treatment fields as are specified by the radiation-treatment plan.

8 Claims, 3 Drawing Sheets

METHOD AND APPARATUS PERTAINING TO OPTIMIZING A RADIATION-TREATMENT PLAN BY PERMITTING NON-COINCIDENTAL ISOCENTERS

CROSS-REFERENCE TO RELATED APPLICATION

This application is a continuation of prior U.S. patent application Ser. No. 15/080,685, filed Mar. 25, 2016, which is incorporated herein by reference in its entirety.

TECHNICAL FIELD

This invention relates generally to radiation-treatment planning.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted structures and adjacent tissues, organs, or the like that are desired or even critical to continued survival of the patient. As a result, radiation is ordinarily applied in a carefully administered manner to at least attempt to restrict the radiation to a given target volume.

Many treatment plans provide for exposing the target volume to radiation from a number of different directions. Arc therapy, for example, comprises one such approach. In such a case it often becomes useful or necessary to adjust the radiation-treatment platform to accommodate various differences that occur or accrue in different fields when moving the radiation source with respect to the target volume. A radiation-treatment plan therefore often provides information regarding useful or necessary adjustments to the radiation-treatment platform during such a treatment.

For ease of planning and implementation, in many cases the radiation beam is flattened using one or more flattening filters. Notwithstanding this flattening, a typical treatment plan endeavors to ensure that the isocenter of each administered beam is the same (and typically in the center of the beam) regardless of the administration angle and other field considerations. Unfortunately, this often leads to higher intensity in the middle of the planned treatment volume and a resultant wasting of energy in order to assure the right overall dose distribution.

BRIEF DESCRIPTION OF THE DRAWINGS

The above needs are at least partially met through provision of the method and apparatus pertaining to optimizing a radiation-treatment plan by permitting non-coincidental isocenters described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit utilizes patient information and treatment-platform information to optimize a radiation-treatment plan by permitting isocenters of various radiation-treatment fields as comprise parts of a same treatment plan to not be coincidental with one another to thereby yield an optimized treatment plan. The patient information can pertain to one or more physical aspects of the patient as desired.

By one approach, the foregoing can comprise scattering the isocenters of the various radiation-treatment fields around a predetermined point (such as, for example, the center of the treatment volume). To put this another away, this approach can comprise causing an area of highest energy flux for a given field to be non-coincident with at least some of the other radiation-treatment fields that are also specified by the radiation-treatment plan.

The aforementioned radiation-treatment plan can comprise, by one approach, an intensity-modulated radiation-therapy plan. This can include intensity-modulated radiation-therapy plans that presume nonuse of a radiation beam-flattening filter.

So configured, a desired dosage distribution can often be attained in a more efficient manner (i.e., with less energy wastage) than has been achieved in the past with traditional approaches that seek to ensure that the beam isocenters for various fields as collectively comprise a radiation-treatment session are fully or at least substantially coincident with one another. For that matter, the corresponding calculations to form such a plan are not unduly complicated nor likely to significantly extend the amount of time a given plan-optimization methodology may require to iterate and identify a resultant plan.

Figure 1:
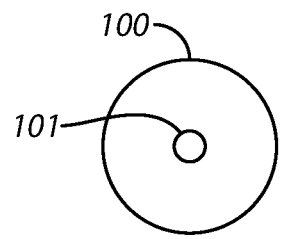
FIG. 1 comprises a schematic representation as configured in accordance with the prior art.

These and other benefits may become clearer upon making a thorough review and study of the following detailed description. First, however, it may be useful to first recount in more detail certain elements of past practice in these regards. FIG. 1 illustrates, for example, a treatment volume 100 (such as a patient's organ, tumor, or tissue of concern) undergoing radiation treatment. In this simple example, the isocenter 101 of the radiation beam for each treatment field is the same. (The isocenter is the point in space through which the central ray of the radiation beams pass.) Accordingly this isocenter 101 is both the radiation isocenter (i.e., the center of the beam) and also the mechanical isocenter (i.e., the point where the center rays of the radiation beams for all of the treatment fields intersect).

Figure 2:
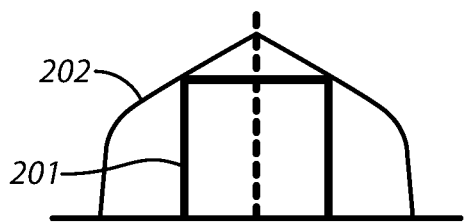
FIG. 2 comprises an energy flux profile as configured in accordance with the prior art.

FIG. 2, in turn, depicts an energy flux profile 202 across a prior-art radiation beam (presuming a flattening-filter-free mode of operation). The actual shape will of course depend on the energy used and the point where the flux profile (at the location where the total ascension is largest) begins to decrease rapidly (i.e., the so-called field edge) (to, for example, around thirty to sixty percent of the peak value). In this illustrated example the required energy fluence 201 is flat. As a result, the extra flux will typically be blocked using jaws, one or more multi-leaf collimators, or the like.

Figure 3:
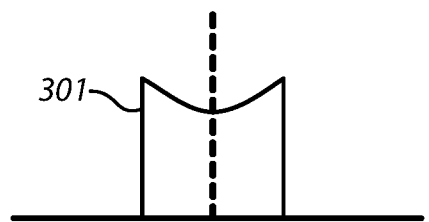
FIG. 3 depicts an opening ration matrix as configured in accordance with the prior art.

FIG. 3 depicts a corresponding opening ratio matrix 301. In order to produce such a shape with a single collimator leaf-pair, the two peaks will typically be formed separately. This, in turn, typically leads to a lost monitor unit (MU) factor of about 1.2 that is attributable to the amount of the total ascension of the opening ratio matrix 301 curve.

Figure 4:
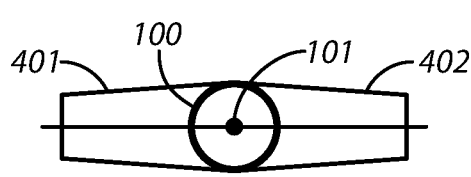
FIG. 4 comprises a side-elevational schematic representation as configured in accordance with the prior art.
Figure 5:
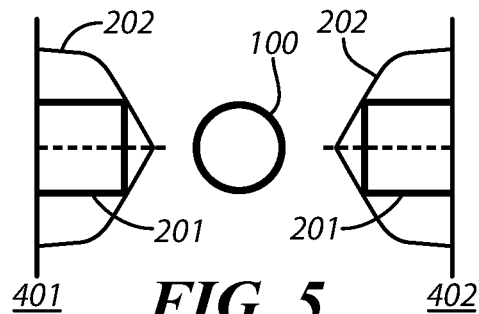
FIG. 5 depicts energy flux profiles as configured in accordance with the prior art.

With the foregoing in mind, FIG. 4 exemplifies a simple intensity-modulated radiation-therapy (IMRT) treatment that comprises a first radiation beam 401 and a second, opposing radiation beam 402. The illustrated example typifies prior art practice in these regards and hence the two beams 401 and 402 share a common isocenter 101 that is, in turn, located at the center of a planned treatment volume 100. FIG. 5 illustrates the required energy fluxes 202 to produce a flat dose distribution within this planned treatment volume 100. (Those skilled in the art will note that there are some degrees of freedom to split the flux between these two fields, but the illustrated example represents a typical view of a most-efficient configuration in these regards.)

Figure 6:
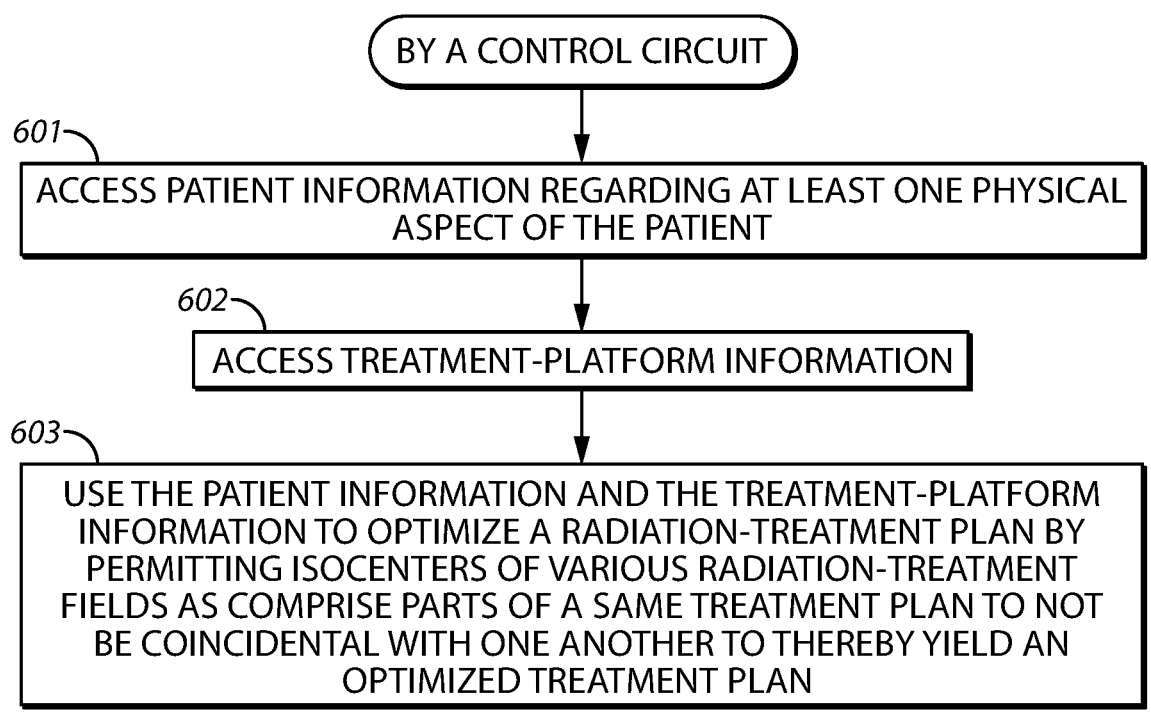
FIG. 6 comprises a flow diagram as configured in accordance with various embodiments of the invention.

Referring now to FIG. 6, an illustrative process 600 that runs contrary to many of the key presumptions of the foregoing will be presented. This process 600 can be carried out, for example, by a control circuit of choice. Further elaboration in those regards will be provided below.

At step 601, this process 600 provides for accessing patient information regarding at least one physical aspect of a given patient. The specific nature of the patient information can of course vary from patient to patient and with respect to the nature of the patient's treatment requirements. Examples include but are not limited to information regarding the patient's geometry (or sub-geometry as pertains to portions of interest), physical orientation, and the relative positions of specific organs, tissues, and biological subsystems, to note but a few. This patient information can include relatively static information that does not change much over time as well as relatively dynamic information that changes slowly or quickly over time (such as a growing or shrinking tumor on the one hand or an expanding/contracting lung on the other hand). As the present teachings are not especially sensitive to requiring any particular patient information, further elaboration in these regards will not be presented here.

At step 602 this process 600 also provides for accessing treatment-platform information. This information, too, can vary with the application setting. Examples in these regards include details regarding the nature and strength of the radiation source, dimensions and details regarding a gantry that holds and transports the radiation source during a treatment session, the number, type, and capabilities of collimators, jaws, and the like as may be available, the dimensions and orientation of the patient-support surface, and so forth. Again the present teachings are not overly sensitive to any particular choices in these regards and therefore further details will not be provided here for the sake of brevity and clarity.

At step 603, this process 600 then uses the foregoing patient information and treatment-platform information to optimize a radiation-treatment plan by permitting isocenters of various radiation-treatment fields as comprise the parts of a same treatment plan to not be coincidental with one another to thereby yield an optimized treatment plan. (It will be understood that the expression "optimizing" should not be confused with the idea of identifying an objectively "optimum" plan that is superior to all other possible plans. Instead, such optimization comprises iteratively assessing alternatives to a given plan to typically identify a series of successively-better plans.)

As used herein, this reference to not being "coincidental" can refer, by one approach, to being completely non-coincidental. In this case the isocenters of at least certain beams are completely exclusive of one another. These teachings are not limited in these regards, however. Accordingly, if desired, this reference to not being "coincidental" can include not being substantially coincidental. In this case the isocenters of certain beams may be, for example, partially overlapping with one another but not more than, say, ten percent overlapping, twenty-five percent overlapping, forty percent overlapping, fifty percent overlapping, sixty percent overlapping, or some other figure of merit as desired.

By one approach, this step of permitting isocenters of various radiation-treatment fields to be non-coincidental can comprise scattering those isocenters around, for example, a predetermined point (such as the center of the planned treatment volume). In any event, by permitting (or in fact requiring) these isocenters to be non-coincidental with one another, this step provides for causing an area of highest energy flux for a given field to be non-coincident for at least some of the other radiation-treatment fields of that same treatment plan.

Figure 7:
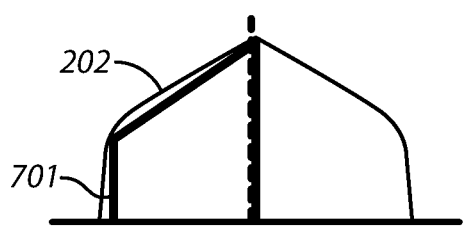
FIG. 7 comprises an energy flux profile as configured in accordance with various embodiments of the invention.
Figure 8:
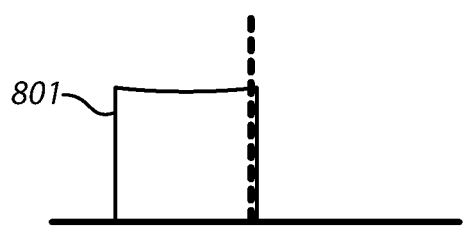
FIG. 8 depicts an opening ratio matrix as configured in accordance with various embodiments of the invention.

FIGS. 7 and 8 provide illustrative examples in these regards. These figures illustrate, for example, an energy fluence 701 and an opening ratio matrix 801 that comport with these teachings and that are very different from the prior art approach typified in FIGS. 2 and 3. Here, and as a result of scattering the aforementioned isocenters as described, the central minimum in the opening ratio matrix 801 has nearly disappeared (especially when compared to the opening ratio matrix 301 shown in FIG. 3). As a result, those skilled in the art will understand and appreciate that the energy flux is now delivered more efficiently as compared to the previous practices described above.

Figure 9:
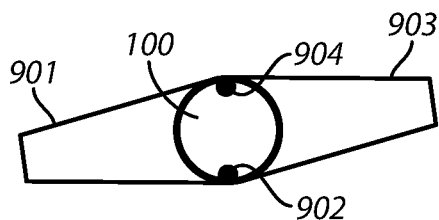
FIG. 9 comprises a side-elevational schematic representation as configured in accordance with various embodiments of the invention.
Figure 10:
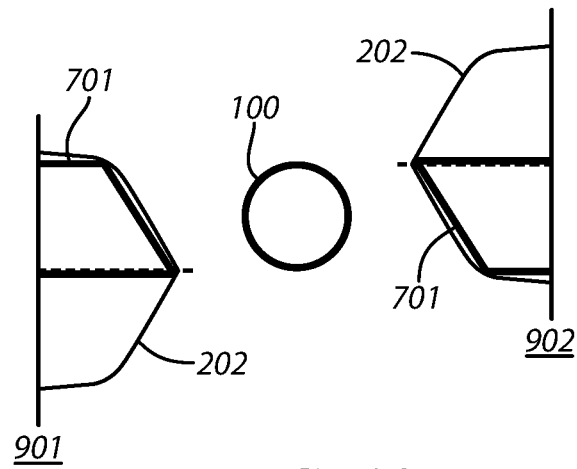
FIG. 10 depicts energy flux profiles as configured in accordance with various embodiments of the invention.

FIGS. 9 and 10 provide a further illustrative example in these regards. As with the example provided earlier (with respect to FIGS. 4 and 5), these examples presume a simple IMRT treatment employing two opposing beams 901 (having a corresponding isocenter 902) and 903 (having a corresponding isocenter 904). This example clearly illustrates the use of non-coincident isocenters 902 and 904. The required flux 701 and 702, in turn, is divided as shown in FIG. 10 to yield more efficient opening ratio matrixes.

Figure 11:
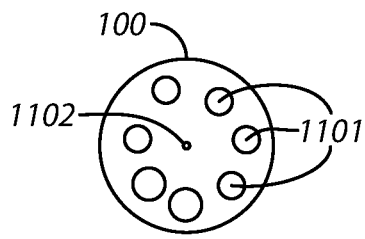
FIG. 11 comprises a schematic representation as configured in accordance with various embodiments of the invention.

FIG. 11 provides a multi-field-based view of a planned treatment volume 100 where each field has a corresponding isocenter 1101 that is fully non-concentric with all other field isocenters 1101 and where those isocenters 1101 are themselves scattered more or less equally about a central point 1102. By scattering these isocenters 1101 for these various fields as comprise the radiation treatment in this way, the central maxima of the fields do not all meet at a common isocenter. Instead, the resulting dosage is distributed considerably more evenly across the planned treatment volume 100.

There are various ways by which this scattering of the isocenters 1101 from one field to another (or at least for some of the fields) can be accomplished. By one approach, for example, the patient-support surface (such as a couch) can be selectively shifted slightly in-between at least some of the radiation pulses.

In any event, and generally speaking, by properly scattering the isocenters for at least some of the fields during a single treatment session, the conical shape of a flattening-filter-free beam can be utilized in conjunction with IMRT optimization without tending towards the creation of flat fluences.

Figure 12:
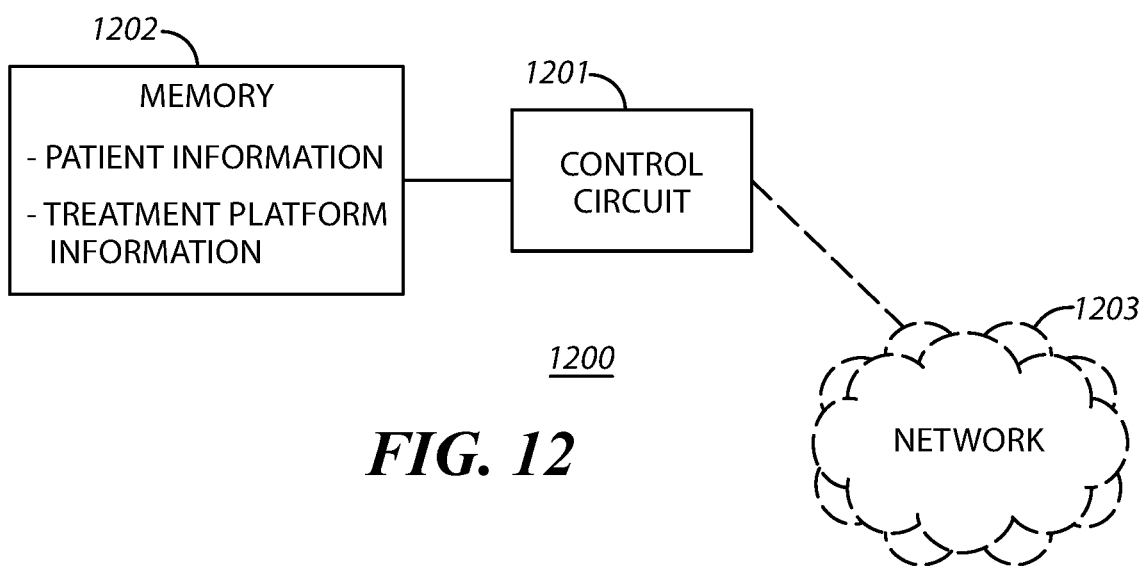
FIG. 12 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 12, an illustrative approach to such a platform will now be provided.

In this illustrative example the platform 1200 includes a control circuit 1201 that operably couples to a memory 1202. Such a control circuit 1201 can comprise a fixed-purpose hard-wired platform or can comprise a partially or wholly programmable platform. These architectural options are well known and understood in the art and require no further description here. This control circuit 1201 is configured (for example, by using corresponding programming as will be well understood by those skilled in the art) to carry out one or more of the steps, actions, and/or functions described herein.

The memory 1202 may be integral to the control circuit 1201 or can be physically discrete (in whole or in part) from the control circuit 1201 as desired. This memory 1202 can also be local with respect to the control circuit 1201 (where, for example, both share a common circuit board, chassis, power supply, and/or housing) or can be partially or wholly remote with respect to the control circuit 1201 (where, for example, the memory 1202 is physically located in another facility, metropolitan area, or even country as compared to the control circuit 1201).

This memory 1202 can serve, for example to store the aforementioned patient information and/or treatment-platform information. This memory 1202 can also serve to non-transitorily store the computer instructions that, when executed by the control circuit 1201, cause the control circuit 1201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

If desired, such a platform 1200 can further include one or more user interfaces (not shown) of choice (including user-input mechanisms and/or user-output mechanisms of choice). If desired, the control circuit 1201 can also be configured to communicate compatibly with one or more networks 1203 of choice including but not limited to the Internet.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As but one example in these regards, these teachings could be employed with only a single field. As an example of a single field case, an arc field could have its isocenter location altered during gantry rotation by synchronized couch movements. Somewhat similar results could be achieved by dividing one arc in multiple arcs with different isocenters.

We claim:

1. A method comprising:
at a control circuit:
    accessing patient information regarding at least one physical aspect of the patient;
    accessing treatment-platform information;
    using the patient information and the treatment-platform information to optimize a radiation-treatment plan by permitting isocenters of various radiation-treatment fields, which various radiation-treatment fields comprise parts of a same treatment plan, to not be coincidental with one another to thereby yield an optimized treatment plan, wherein permitting the isocenters of various radiation-treatment fields to not be coincidental with one another comprises, at least in part, scattering the isocenter of at least one of the various radiation-treatment fields with respect to a predetermined point.

2. The method of claim 1 wherein the radiation-treatment plan comprises an intensity-modulated radiation-therapy (IMRT) plan.

3. The method of claim 2 wherein the IMRT plan presumes nonuse of a radiation beam-flattening filter.

4. The method of claim 1 wherein scattering the isocenter of at least one of the various radiation-treatment fields around a predetermined point comprises scattering the isocenters of at least some of the various radiation-treatment fields around a predetermined point.

5. An apparatus comprising:
    a memory having patient information regarding at least one physical aspect of the patient and treatment-platform information stored therein;
    a control circuit operably coupled to the memory and configured to:
        access the patient information and the treatment-platform information;
        use the patient information and the treatment-platform information to optimize a radiation-treatment plan by permitting isocenters of various radiation-treatment fields, which various radiation-treatment fields comprise parts of a same treatment plan, to not be coincidental with one another to thereby yield an optimized treatment plan, wherein permitting the isocenters of various radiation-treatment fields to not be coincidental with one another comprises, at least in part, scattering the isocenter of at least one of the various radiation-treatment fields with respect to a predetermined point.

6. The apparatus of claim 5 wherein the radiation-treatment plan comprises an intensity-modulated radiation-therapy (IMRT) plan.

7. The apparatus of claim 6 wherein the IMRT plan presumes nonuse of a radiation beam-flattening filter.

8. The apparatus of claim 5 wherein the control circuit is configured to scatter the isocenter of at least one of the various radiation-treatment fields around a predetermined point by scattering the isocenters of at least some of the various radiation-treatment fields around a predetermined point.

* * * * *

UNITED STATES PATENT AND TRADEMARK OFFICE
CERTIFICATE OF CORRECTION

PATENT NO. : 10,549,119 B2
APPLICATION NO. : 16/255086
DATED : February 4, 2020
INVENTOR(S) : Viljo Petäjä, Perttu Niemelä and Esa Kuusela Page 1 of 1

It is certified that error appears in the above-identified patent and that said Letters Patent is hereby corrected as shown below:

On the Title Page (*) Notice: After "days." insert --This patent is subject to a terminal disclaimer.--.
(45) Date of Patent: Before Feb. 4, 2020 insert --*--.

Signed and Sealed this
Seventh Day of April, 2020

Andrei Iancu
*Director of the United States Patent and Trademark Office*